United States Patent [19]

Nardella

[11] Patent Number: 5,341,807
[45] Date of Patent: Aug. 30, 1994

[54] ABLATION CATHETER POSITIONING SYSTEM

[75] Inventor: Paul C. Nardella, North Easton, Mass.

[73] Assignee: American Cardiac Ablation Co., Inc., Taunton, Mass.

[21] Appl. No.: 906,529

[22] Filed: Jun. 30, 1992

[51] Int. Cl.[5] ............................................. A61B 5/04
[52] U.S. Cl. ..................................... 128/642; 606/38; 606/41; 607/116
[58] Field of Search ................ 128/642, 693, 734, 737, 128/783–786, 804, 695; 606/32–38, 41, 49, 46; 607/115, 116, 119–122, 125

[56] References Cited

U.S. PATENT DOCUMENTS

| | | | |
|---|---|---|---|
| 4,540,002 | 9/1985 | Atlas | 128/734 |
| 4,630,615 | 12/1986 | Yomtov | 128/734 |
| 4,641,649 | 2/1987 | Walinsky et al. | 128/804 |
| 4,721,115 | 1/1988 | Owens | 128/713 |
| 4,729,385 | 3/1988 | Juncosa et al. | 128/734 |
| 4,785,815 | 11/1988 | Cohen | 128/642 |
| 4,905,696 | 3/1990 | Amundson et al. | 128/419 PG |
| 4,911,174 | 3/1990 | Penderson | 128/695 |
| 4,945,912 | 8/1990 | Langberg | 128/642 |
| 4,947,857 | 8/1990 | Albert et al. | 128/696 |
| 4,985,028 | 1/1991 | Ismar et al. | 606/15 |
| 5,022,396 | 6/1991 | Watanabe | 128/642 |
| 5,025,794 | 6/1991 | Albert et al. | 128/696 |
| 5,078,714 | 1/1992 | Katims et al. | 606/38 |
| 5,109,870 | 5/1992 | Silny et al. | 128/780 |
| 5,121,750 | 6/1992 | Katims | 128/734 |
| 5,156,151 | 10/1992 | Imran | 128/642 |

*Primary Examiner*—Stephen G. Pellegrino
*Assistant Examiner*—M. Peffley
*Attorney, Agent, or Firm*—Lahive & Cockfield

[57] ABSTRACT

A multi-electrode cardiac catheter has pairs of electrodes connected to sensing circuitry to produce a differential signal. The sensing output is sharply defined and self-normalizing. Preferably a catheter ablation tip electrode is an electrode of one pair, and the differential signal becomes non-zero when the tip contacts surrounding tissue. The shape of the differential signal provides information on the degree of electrode contact, as well as on the on the amount of locally-sensed tissue impedance change. The signal may be used as a trigger enable signal for a cardiac ablation catheter, and the applied level of RF power may be controlled based on the indicated degree of electrode contact and value of tissue impedance.

13 Claims, 4 Drawing Sheets

ABLATION CATHETER POSITIONING SYSTEM

The present invention relates to electrode-bearing catheters, and more particularly to catheters of the type which are inserted along a blood vessel in order to position its electrodes in the region of a patient's heart. The electrodes may be used for sensing cardiac electrical signals, applying electrical stimulation for diagnostic testing or the like, or applying treatment signals, such as tissue ablation signals. The catheter may include other structures, such as a lumen and a delivery system, for applying light, thermal energy or chemical agents, or a sampling system for sampling tissue, forming images of tissue or withdrawing a specimen of the surrounding fluid.

To position such an electrode-bearing catheter at a desired site within the patient's body, one or more catheter insertion and radiographic visualization steps are usually required in the course of bringing the catheter to its general target area. Once the catheter has been placed in position, further control and interaction by the surgeon is generally required to assure that the catheter is precisely positioned and properly oriented to perform its intended functions.

For example, when the catheter is an RF tissue ablation or coagulation treatment catheter, it may be necessary to perform various preliminary electrical measurements or mapping operations to assure that the power electrode has moved into contact with a specific tissue region that is to be treated, such as a cardiac lesion, that is initiating arrhythmias.

Among the prior art known to applicant, one cardiac catheter of this type is configured as a special purpose mapping catheter, and utilizes a multi-electrode structure to generate characteristic tissue impedance responses at different tissue sites, from which the relative position of the catheter can be determined. Specifically, U.S. Pat. No. 4,911,174 shows such an electrode structure wherein the impedance is measured by successive pairs of electrodes to detect when an electrode has advanced beyond a blood/tissue interface. An abrupt shift in phase of the detected impedance is noted at the electrode positioned by the interface. The device of that patent appears to be intended for the very specific purpose of determining the size of a patient's ventrical, or more precisely, positioning a catheter having a plurality of surface ring electrodes in the ventrical in such a way that the relative locations of the electrodes are known and it becomes possible to map an impedance distribution from which ventricle volume is derived.

Other forms of catheter impedance measurement are known, generally involving the measurement of localized or whole body impedance paths for the purpose of setting or controlling the level of power delivery of an RF coagulation electrode during electrosurgery. To applicant's knowledge such systems have no application to catheter positioning.

It is therefore desirable to develop more accurate ways of positioning or orienting a catheter by the use of electrical signals detected at its electrodes.

SUMMARY OF THE INVENTION

It is an object of the present invention to provide a positioning system for a cardiac ablation catheter.

It is another object of the present invention to provide a catheter system useful for mapping and ablation of tissue.

It is another object of the invention to provide an improved system for monitoring electrical activity of cardiac tissue.

These and other desirable objects are achieved in accordance with the present invention by providing a multi-electrode catheter having pairs of electrodes, stimulating at least one pair of the electrodes to provide a sensing signal responsive to regional tissue variations, and combining two or more sensing signals. Preferably the combined sensing signal is a differential signal developed from several sets of electrodes such that the magnitude of the combined signal is null except when two sets of electrodes reside in or near regions of differing tissue type. The circuit connection is such that the signal vanishes when the electrodes all reside in similar tissue environments. By forming a differential signal from multiple sets of electrodes in this way, the invention eliminates the thresholding, normalizing or averaging and other complex signal processing operations formerly necessary to obtain a meaningful impedance measurement. Furthermore, by selection of particular ones of the catheter electrodes for polling, the precise orientation or position of the catheter is determined.

In a preferred embodiment, the catheter is a cardiac ablation catheter having a tip electrode for applying ablation energy to a tissue site. Tissue impedance is measured by applying probe signals between the tip and a downstream electrode, sensing the return current through two or more intermediate ring electrodes located below the tip, and combining the sensed return current to define a differential signal. So long as each electrode resides in blood, the inter-electrode impedance path characteristics of each electrode pair are similar, and after being differentially combined with a gain factor to correct for electrode geometry, they yield a null signal. Thus, the electrode is self-zeroing without calibration in an external saline cell. However, when the catheter resides in a blood vessel and the tip electrode contacts tissue, the differential signal rises sharply. Similarly, should a proximal electrode contact the vessel wall, a similarly discernible signal will occur, but of reversed polarity. The differential output signal thus provides a dependable indication that the catheter has assumed an effective position for applying electrosurgical power.

BRIEF DESCRIPTION OF THE DRAWINGS

The invention will be understood from the description of illustrative embodiments below, taken together with the drawings, wherein.

DETAILED DESCRIPTION OF THE INVENTION

Figure 1:
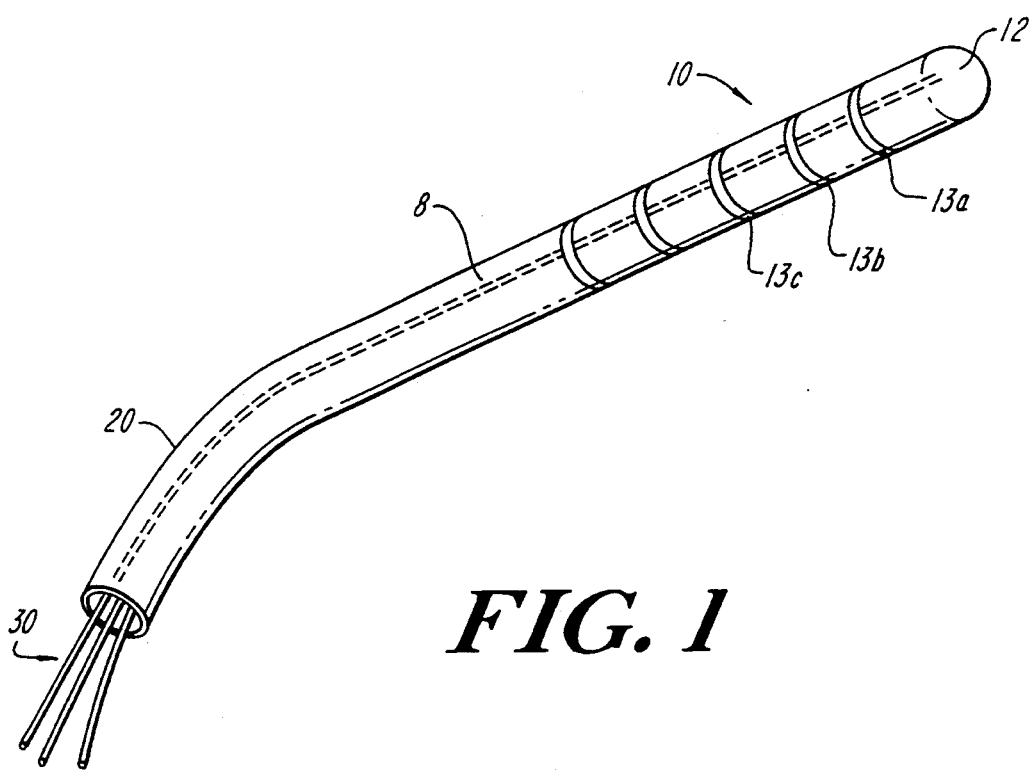
FIG. 1 is a perspective view of a multi-electrode catheter for the practice of the present invention.

A multi-electrode mapping and ablation catheter 10 is shown in FIG. 1, and is characterized by an elongated insulating body 8 having a rounded tip electrode 12 mounted at its tip, and a plurality of axially-spaced ring electrodes 13a, 13b ... mounted along its surface. Each of the ring electrodes has dimensions and an exposed surface area $A_r$ identical to the others, and they are preferably equi-spaced along the body 8. The tip electrode 12, which may also take other forms, such as a split wire, or bipolar electrode, has a somewhat larger area $A_t$. Catheter 10 is mounted at the end of a flexible but axially incompressible tube 20 which is used for manipulating and inserting the catheter along a vessel, and a plurality of electrode signal leads 30 extend from the various electrodes, through the catheter body 8 and tube 20 to a control circuit located outside the body. Leads 30 allow each electrode to be separately connected to the control circuit or they may be connected to sense the propagation of the tip electrode signal.

For example, tip electrode 12 may be connected to a relatively strong source of RF power which is adjustably controlled to perform tissue ablation, or is operated at a lower level to provide a monitoring signal for determining tissue impedance measurements. Ring electrodes 13a, 13b . . . are connected to sensing and signal processing circuitry for sensing muscle discharge potentials and mapping the locations of cardiac lesions or arrhythmia-generating nodes.

In a conventional mapping protocol, the catheter may be slowly advanced along an intracardial vessel, and local arrhythmias stimulated by a pulse signal emitted at the tip electrode may be detected and mapped by an analysis of the signal as detected at each of the plurality of ring electrodes. Once a tissue site responsible for initiating an arrhythmia is mapped, the catheter is then repositioned to coagulate the arrhythmia site by placing the tip in contact with the site and applying an RF signal of effective tissue coagulating power thereto.

In using a multi-electrode mapping probe in this manner to first identify and then coagulate unhealthy tissue, it is necessary that the tip electrode 12 be contacting, or at least in very close proximity to the target tissue site. This is because the region of effective RF power delivery drops off sharply away from the immediate surface of the treatment electrode. Moving tip 12 even a few millimeters away from a tissue site can reduce the applied energy to an ineffective level, or can cause coagulation of blood to occur in the vessel rather than ablation of adjacent tissue.

Figure 2:
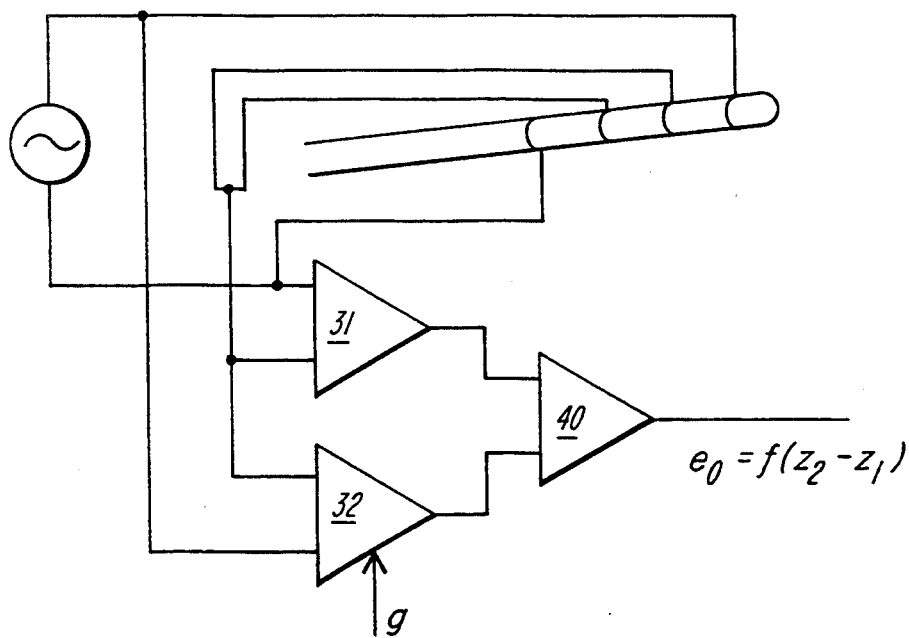
FIG. 2 and 3 show catheter signal coupling arrangement for the practice of the present invention.

In accordance with the present invention, the relative position of a probe is determined with respect to surrounding tissue by applying a test signal, for example, a continuous-wave, low power, AC signal, between a pair of outer electrodes arrayed along the catheter, and pairing each outer electrode with an inner electrode to develop a sensing signal characteristic of impedance for the tissue between the electrodes. By "outer" is meant an electrode which lies axially at one extreme of a set of the electrodes. Thus, in FIG. 2, showing the tip electrode and successive first, second and third ring electrodes, the tip electrode and the third ring electrode are the outer electrodes of the set, and an AC pulse signal is applied between these two electrodes to establish an impedance chain or bridge extending through the tissue spanning all of the intermediate electrodes. Thus, the tissue acts as an impedance dividing bridge, allowing local impedance to be sensed between any pair of intermediate electrodes.

As shown in FIG. 2, signal amplifiers 31, 32 are each connected to one pair of electrodes to develop a signal that is essentially proportional to the product of the electrode area times a function of the impedance of tissue lying between the two electrodes of the pair. A normalizing gain 9 is applied to one amplifier, preferably to amplifier 32, to correct by a scale factor the contribution of the larger (tip) electrode. This gain is a constant that, for a given general probe size and shape, depends only on the relative area and spacing of electrode 12, and may be readily set, for example, when the electrodes are immersed in a sample saline solution. The gain factor normalizes the amplifier outputs, so that when both pairs of electrodes are immersed in the same tissue, e.g., blood, the outputs of the respective amplifiers will be equal. The outputs of both amplifiers 31, 32 are applied as the inputs to a final or second stage amplifier 40. Amplifier 40 produces an output signal proportional to the difference in the signal potentials appearing at its input terminals, so that it has a net output only when the outputs of amplifiers 31, 32 differ, i.e., when different tissue types are positioned near to the two different electrode pairs, producing distinctly different sets of impedance paths.

Figure 2A:
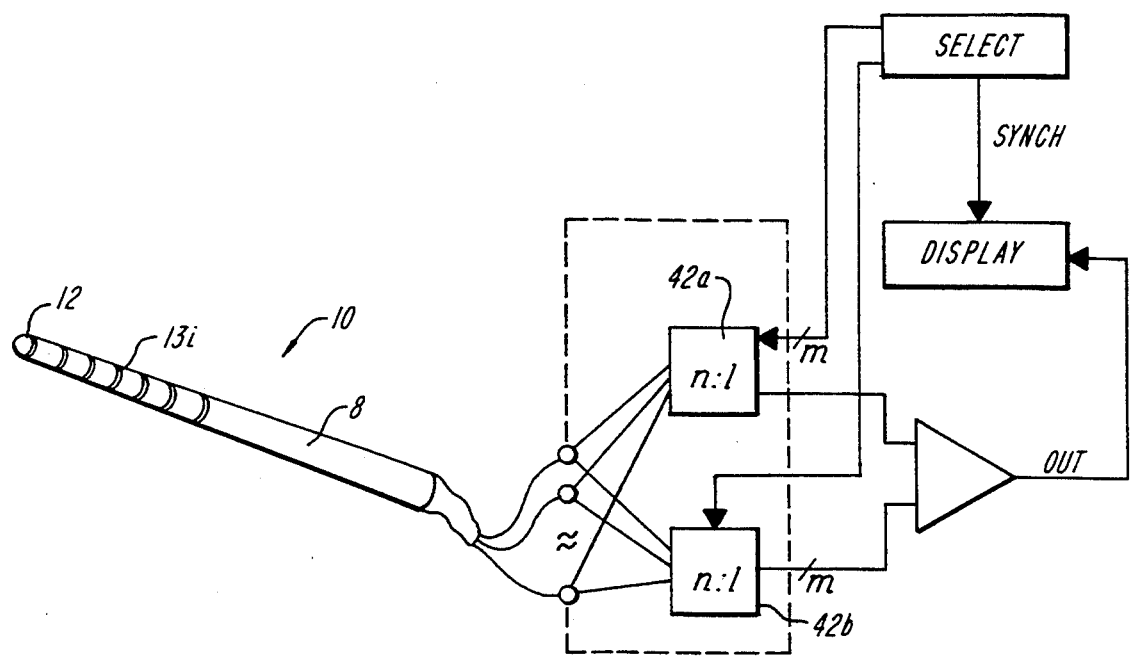
FIG. 2A shows a detail of electrode signal sampling circuitry.

Preferably, as shown in FIG. 2A, the apparatus further comprises a multiplex switch 42a, 42b which operates, either with manual selection by a user, or preferably as shown under program control by a state selector 43 to selectively connect the differential impedance sensing circuitry to different pairs of the catheter electrodes 13i, 13k. By coupling the state of the multiplex switch 42a, 42b to a suitable display, the system indicates detection, for example, of tissue impedance changes that occur within a region spanned by an arbitrary one of the sensing electrode pairs, rather than simply the frontmost pair as described above for the sensing electrode configuration of FIGS. 1 and 2.

Switching unit 42a, 42b may also be controlled to vary the spatial resolution of the impedance detection circuitry, by selecting the sensing signals across pairs of electrodes that are separated from each other by one or more electrodes, or the signals from two pairs of electrodes wherein the electrodes of one pair are spaced from the electrodes of the other pair by one or more intervening ring electrodes 13.

An alternative construction (not illustrated) dispenses with the switching unit 42a, 42b, and directly attaches each pair of adjacent electrodes to its own amplifier, with each adjacent pair of amplifiers having its outputs fixedly attached to a second stage amplifier. In that embodiment, an output switching unit 42c may be employed to sample the outputs of either the first stage or the second stage amplifier, rather than to switch the electrodes between inputs of the first stage amplifiers. This alternative construction, while lacking the flexibility to monitor an impedance path extending between widely-separated ring electrodes, may quickly identify the precise region of tissue change.

Figure 3:
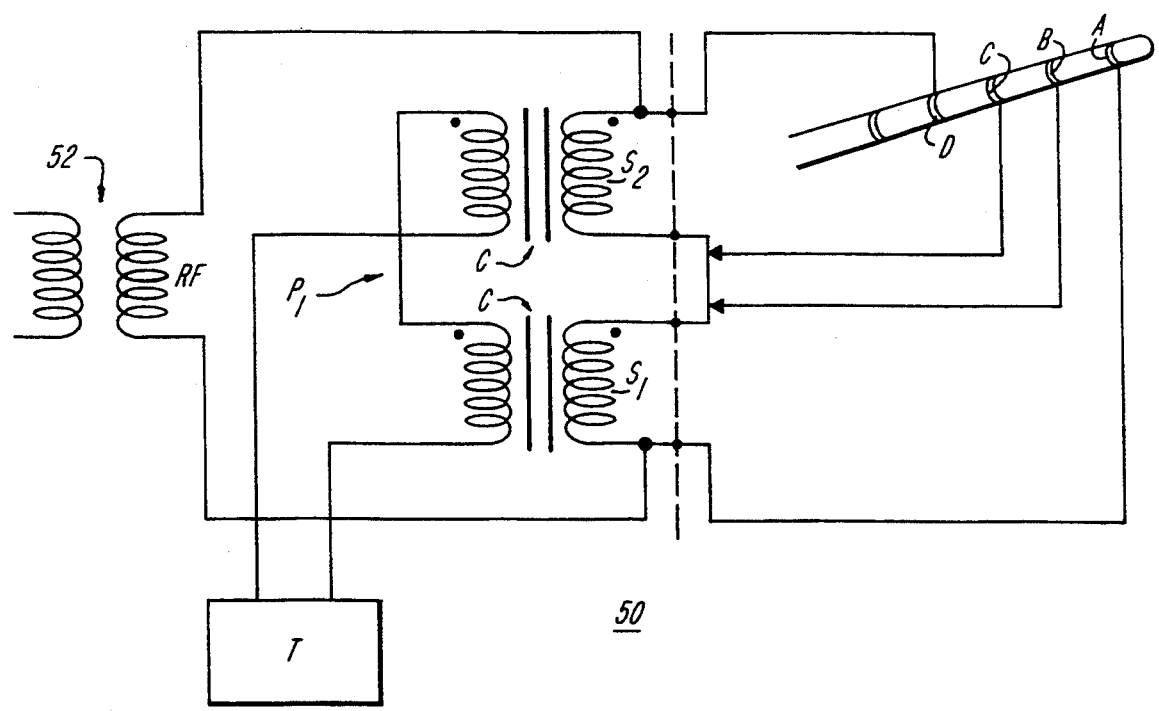

FIG. 3 shows an alternative circuit for the practice of the present invention. The probe 10 is illustrated schematically, with only the tip and three ring electrodes shown. The ring electrodes may, for example, be the first, second and third rings, or first, second and fourth rings, or first, third and fourth, or any three rings spaced in order along the catheter. They are therefore simply labeled A, B, C and D to indicate their order of appearance along the catheter axis, for clarity of discussion. An RF generator 52 is transformer coupled to the probe across the outer electrodes, to apply a biologically safe probe signal at a level of approximately two volts RMS. In this embodiment, a first pair of electrodes, A and B, are connected to a current transformer winding $S_1$, and a second pair of electrodes, C and D, are connected to a separate winding $S_2$ in the opposite sense. A common primary winding or series connected pair of windings, denoted P in FIG. 3, is magnetically coupled via transformer core C to the electrode sensing windings $S_1$ and $S_2$ so that the winding P develops a signal which is essentially a phase-delayed multiple of the difference in the electrical signal sensed by the two electrode pairs. The sensing windings $S_i$ for all adjacent ring electrodes $13_i$, $13_{i+1}$, are all similar, but the sensing winding $S_t$ attached to tip electrode 12 preferably is wound such that the ratio of the number of turns in the winding $S_t$ to those in winding $S_i$ is inversely proportional to the effective areas of the respective electrode pairs, times a distance factor reflecting the geometry and spacing of the irregularly spaced tip electrode from the ring electrode with which it is paired. The winding ratio is selected so that the sum of the sense and anti-sense impedance signals in coils $S_t$, $S_i$ is nominally zero when both pairs of electrodes are fully immersed in blood.

As shown, transformer winding P is connected to a discrimination/control circuit T, which may, for example, integrate the magnitude of the signal detected across winding P and put out a trigger enable signal when the integrated value exceeds a predetermined threshold indicative of electrode tissue contact. Alternatively, circuit T may put out a normalized sense impedance value, which may serve as a basis for determining the relative disposition of the catheter or the type of tissue which surrounds or contacts the catheter. It will be understood that the circuit of FIG. 2A may also be employed in a transformer coupled circuit of this type. In that case, it is preferable to have the multiplex switching units selectively connect the catheter electrode pairs to the transformer sensing coils in an arrangement whereby plural different electrodes are selectively connected to a single pair of windings of one coupling transformer.

Figure 4:
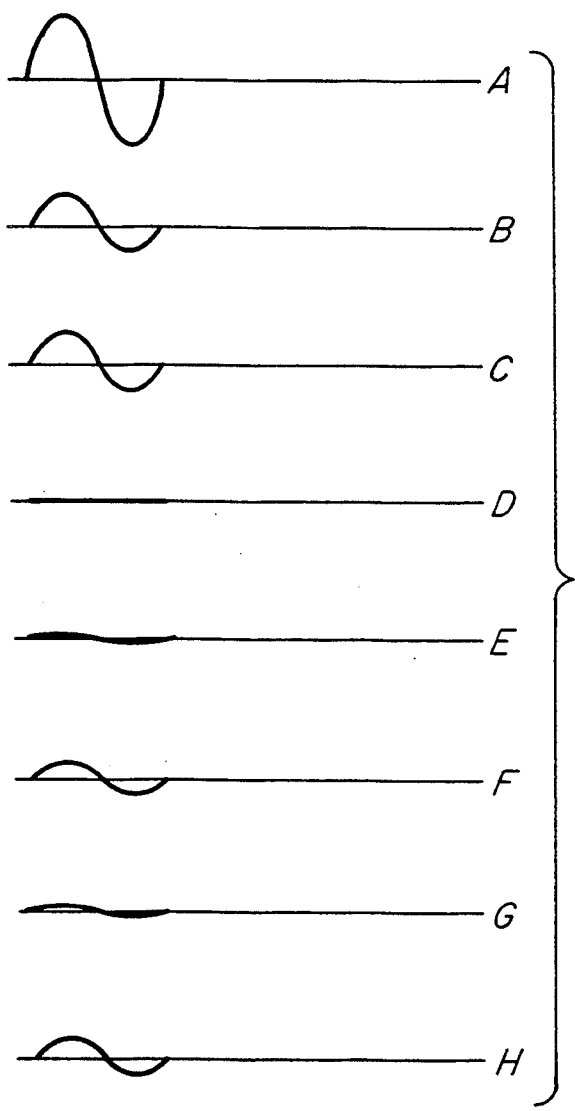
FIG. 4 shows a representative catheter signal traces.

FIG. 4 shows typical signal traces of a signal when all of the sampled electrodes are disposed in a homogeneous medium, as detected between electrodes A, B (trace A of the Figure), and electrodes C, D (trace B of the Figure). Trace C shows the signal of trace A normalized by a constant scale factor to correct for the different area and spacing of tip electrode A, and trace D shows the combined signal, as appearing, for example across the winding P of the transformer in FIG. 3 or the output stage amplifier 40 of FIG. 2.

Traces E-H of FIG. 4 show the signals corresponding to those of traces A-D, respectively, when the catheter has moved to a position such that the body of the catheter resides in blood, but tip electrode 12 (FIG. 1) has been brought into close proximity or contact with a vessel wall or heart muscle tissue. As illustrated, the combined output signal (trace D or H) becomes non-null and develops a discernible peak, upon contact of the tip with heterogeneous tissue. This peak is more or less well-defined, depending upon the degree of proximity to, or area of contact between, electrode 12 and the surrounding tissue structures.

It will be understood that the non-zero differential sensing peak need not be a positive-valued signal as shown, but may include negative dips or have some other shape or polarity, caused by phase inversion or the like which occurs as a consequence of the locally varying tissue structures. Further, it will be understood that the sensed signals need not be fully representative of the tissue impedance function, but rather are sensed signals from which impedance is derivable. For example, when impedance itself is to be monitored in order to determine a substantive physical property of the surrounding tissue, e.g., the type of tissue or its degree of coagulation, the instantaneous voltage and current of an electrode pair may be sampled, processed and compared to an RF probe signal that has been applied by signal generator 50 (FIG. 1), to provide an actual impedance function. In general, however, the benefits of the invention are achieved in simply detecting the magnitude of a well-defined difference signal, lines F-H, when it is only desired, for example, to confirm that tissue contact by the probe tip has occurred.

Figure 5:
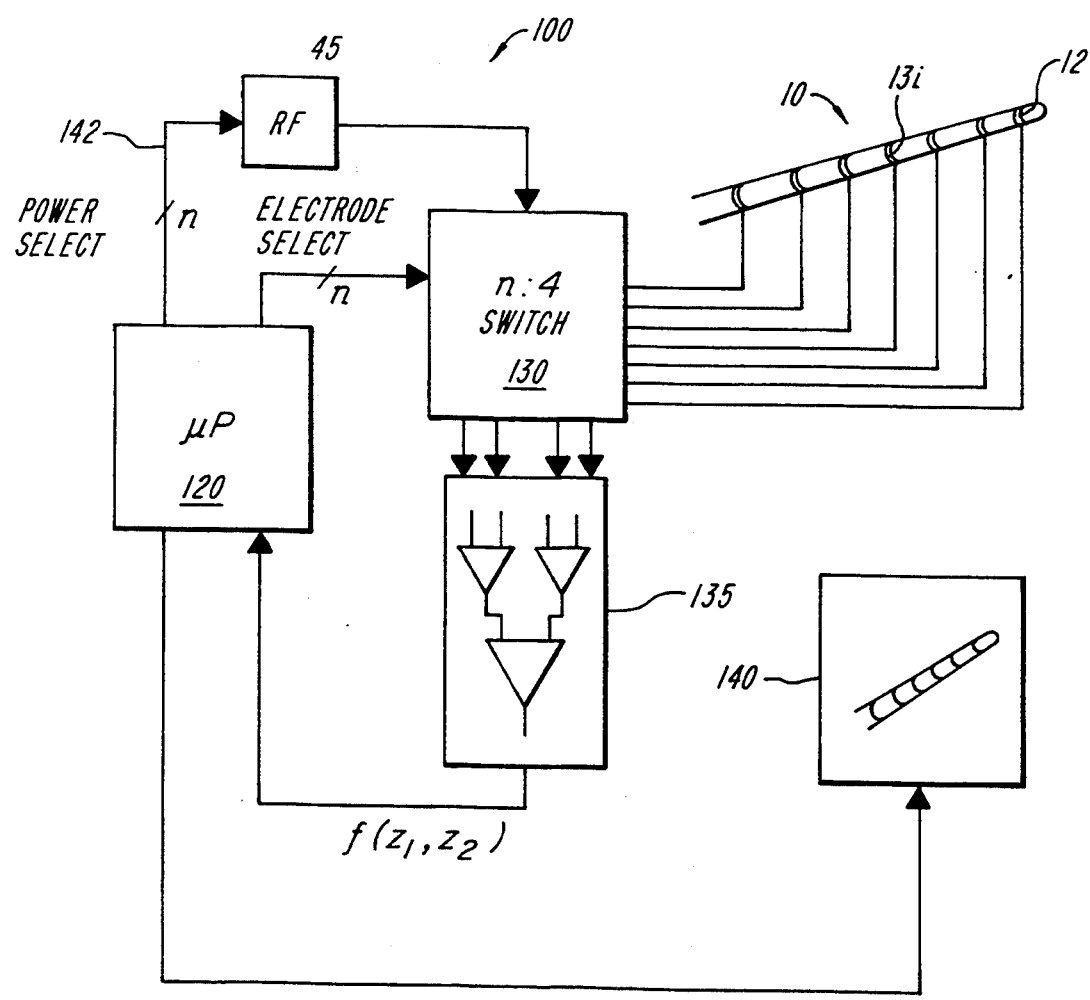
FIG. 5 shows catheter signal processing elements.

FIG. 5 is a schematic block diagram for the operation of a catheter positioning system 100 for controllably positioning an ablation catheter in the cardiac region. As shown in FIG. 5, a processor 120 is interconnected with the sensing and treatment electrodes 12, $13i$ of catheter 10 via a switching unit 130 comparable to switching unit 42a, 42b of FIG. 2A, connected to a signal conditioning circuit 135. Processor 120 controls the switching unit to select spaced electrodes, preferably two pairs as described above, selected from three or more electrodes, for connection to the signal conditioning circuit, and then receives and evaluates the output of the signal conditioning circuit 135 to detect either the presence of a tissue impedance change at a particular selected electrode, or the value of the local tissue impedance. Signal conditioning circuit 135 may include an arrangement of differential amplifiers as described above, and indicated schematically in the Figure. Alternatively, circuit 135 may include circuit elements only for filtering and amplifying the inter-electrode signals. In that case, the outputs of circuit 135 may be digitized and the microprocessor may digitally combine the output signals to obtain a differential impedance function.

In a variation as described above, an alternative embodiment may have its electrodes fixedly connected to an array of differential signal amplifiers. In that embodiment, the outputs of the signal conditioning amplifiers are switchably sampled via an n:4 switching unit under the control of the processor 120 and similar to unit 130, but located between the signal conditioner 135 and processor 120.

In either case, processor 120 correlates the detected electrode signals with particular ones of the electrodes, preferably by polling them in an ordered sequence, and drives and synchronizes a display 140 to represent the detected tissue characteristics. Display 140 may, for example, depict the probe with a variable marker—such as a LED bar display or a plurality of discrete LEDs mounted on a graphic representation of the catheter. The LEDS are actuated by the processor to display the processed information. Specifically, display 140 may show the site along the probe at which the differential impedance change has been detected, by illuminating a LED at that location; or may show which electrodes are in contact with tissue by illuminating a special colored light at the corresponding electrode location. It may also show information such as displaying the relative portion of the probe which has been inserted into the heart. This may be done by selectively illuminating LED markers along that portion of the displayed image of the probe corresponding to one or more detected impedances or signal conditions which indicate that a longitudinally extending region of the probe body has passed a heart valve, or resides inside a closed tissue structure.

Processor 120, in addition to executing one or more logical programs to determine and display probe disposition corresponding to the detected differential electrode signals, preferably is part of a cardiac ablation or electrosurgery control system. In that case the processor also provides a signal along line 142 to the RF power control unit 45 of the system, for controlling the level of power applied to the probe tip. Some forms of coagulation or ablation power control are conventional, for example, programmed control to apply a sufficient power level, based on sensed whole body tissue impedance, to destroy tissue locally at the tip electrode without causing damage to non-involved tissue. In accordance with the coagulation control aspect of the present invention, the processor detects the electrode disposition, and provides a signal to power control unit 45 to adjust the level of localized power based further on the area of contact of the tip electrode, which is derived, by microprocessor 120, from the magnitude of the differential impedance signal. Thus, for example, when the tip achieves only partial contact, as indicated by a detected charge curve that has a sharply defined shape but still has a relatively high impedance value, the ablation power may be reduced from the conventionally-selected level, to a lower level that limits the amount of ablation energy applied to the contact point. Thus, rather than allowing coagulation to extend into the bloodstream as could occur if the power were delivered based on the assumption of full electrode contact to the vessel wall tissue, a smaller pulse of energy is applied to affect only the smaller area of tissue actually contacting the electrode.

Other variations and modifications adapting the differential signal sensing electrodes and system of the present invention to known cardiac mapping or ablation systems and probes will occur to those skilled in the art, and all such variations and modifications are considered to be within the spirit and scope of the invention to which patent rights are sought, as set forth in the claims appended hereto.

What is claimed is:

1. A system for detecting the relative disposition of a catheter assembly inserted along a vessel of a patient, wherein the catheter has a plurality of electrodes spaced successively along its length, such system comprising
    signal applying means adapted to be coupled to said catheter assembly for applying a sensing signal for propagation through tissue extending in a region located about a first pair of electrodes and about a second pair of electrodes which are disposed along said catheter, to produce a sensing output of each pair of electrodes corresponding to a measure of tissue impedance pathways between the electrodes of such pair, and
    means for differently combining the sensing output simultaneously produced by each of the two electrode pairs into a single differential signal indicative of the disposition of said catheter in said vessel with respect to adjacent tissue.

2. The system of claim 1, wherein the means for differentially combining normalizes a value of a sensing output based on electrode geometry such that the differential signal is normally a null signal.

3. The system of claim 1, wherein said means for differentially combining includes current sensing elements for producing an instantaneous current output for each electrode set, and means for functionally combining instantaneous current outputs of different electrode sets.

4. The system of claim 3, wherein said means for functionally combining includes a multi-winding transformer.

5. The system of claim 1, further comprising
    switching means for selectively interconnecting different electrodes of the catheter assembly to the means for differentially combining.

6. The system of claim 1, wherein plural electrodes of said catheter are connected to different sensing circuits, and further comprising
    switching means for selectively sampling outputs of different sensing circuits to determine tissue characteristics associated with different regions along the catheter.

7. The system of claim 1, further comprising
    display means for displaying a representation of the catheter, and
    control means responsive to the differential signal for causing the display means to indicate when a catheter electrode contacts tissue.

8. The system of claim 7, wherein the catheter is a cardiac ablation catheter having an ablation electrode, and the display indicates when the ablation electrode contacts surrounding tissue.

9. The system of claim 8, further comprising means for indicating a degree of electrode contact with surrounding tissue.

10. The system of claim 1, further comprising means for controlling a level of electrosurgical power applied to said catheter in accordance with said differential signal.

11. A system for detecting the relative disposition of a multi-electrode catheter assembly inserted along a vessel of a patient, such system comprising
    signal applying means adapted to be coupled to said catheter assembly for applying a sensing signal for propagation through tissue extending adjacent to both a first electrode pair and to a second electrode pair, each disposed along said multi-electrode catheter, so as to produce first and second sensing outputs across said first and said second electrode pair, respectively, each sensing output corresponding to a measure of local tissue impedance pathways between electrodes of such pair.
    means for combining the sensing output simultaneously produced by each of the two electrode pairs into a signal differential signal,
    said combining means including a first amplifier and a second amplifier for amplifying the sensing output of said first and said second electrode pairs, respectively, and at least one of said amplifiers has a gain selected to produce a normalized signal such that both amplifiers produce outputs of equal magnitude when said first and second electrode pairs are immersed in blood, said combining means combining the outputs of both said first and said second amplifiers into said differential signal so that the differential signal is normally null and varies in accordance with the differences between tissue located immediately adjacent said first electrical pair and tissue located immediately adjacent said second electrode pair.

12. The system of claim 11, wherein one of said amplifiers has a fan inversely proportional to an effective conductive area of an electrode of one of said sets.

13. A catheter positioning system, for a mapping catheter having a plurality of at least three electrodes disposed in an ordered sequence along a segment of the catheter, with conductors extending from the catheter for selectively connecting the electrodes to the system, such system comprising a signal source for providing a signal means for connecting said signal source between two electrodes of said plurality of electrodes, the two electrodes including a least one electrode located at an end of the segment so that the signal propagates through tissue surrounding the catheter, and the tissue forms an impedance-dividing bridge producing detectable signals across each pair of the electrodes disposed along the segment due to propagation of the signal along impedance pathways through tissue adjoining the mapping catheter means for forming a differential signal by combining the detectable signals produced across each of two pairs of electrodes of said multi-electrode catheter, wherein the two pairs of said electrodes include at least one electrode located between ends of the segment, and means for evaluating the differential signal to determine catheter position.

* * * * *

UNITED STATES PATENT AND TRADEMARK OFFICE
CERTIFICATE OF CORRECTION

PATENT NO. : 5,341,807

DATED : August 30, 1994

INVENTOR(S) : Paul C. Nardella

It is certified that error appears in the above-indentified patent and that said Letters Patent is hereby corrected as shown below:

Column 8, line 64, please replace "fan" with --gain--

Signed and Sealed this

Seventeenth Day of March, 1998

Attest:

BRUCE LEHMAN

Attesting Officer

Commissioner of Patents and Trademarks